(12) United States Patent
Culpovich et al.

(10) Patent No.: US 6,551,521 B1
(45) Date of Patent: Apr. 22, 2003

(54) AUTOMATIC ETCHANT REGENERATION SYSTEM WITH HIGHLY ACCURATE SENSOR FOR MONITORING ETCHANT COMPOSITION

(75) Inventors: Philip Culpovich, Monrovia, CA (US); David Flynn, Santa Clarita, CA (US)

(73) Assignee: Oxford Vue, Inc., Arcadia, CA (US)

( * ) Notice: Subject to any disclaimer, the term of this patent is extended or adjusted under 35 U.S.C. 154(b) by 26 days.

(21) Appl. No.: 09/627,086

(22) Filed: Jul. 27, 2000

Related U.S. Application Data

(60) Provisional application No. 60/146,100, filed on Jul. 27, 1999.

(51) Int. Cl.[7] .................................................. B44C 1/22
(52) U.S. Cl. .............................. 216/84; 216/85; 216/83; 399/57; 356/442
(58) Field of Search ................................. 250/343, 339; 356/436, 208

(56) References Cited

U.S. PATENT DOCUMENTS

| | | | | |
|---|---|---|---|---|
| 3,713,743 A | * | 1/1973 | Simms | 356/338 |
| 3,838,925 A | * | 10/1974 | Marks | 356/438 |
| 3,861,802 A | * | 1/1975 | Belmear, Jr. | 356/442 |
| 4,132,585 A | * | 1/1979 | Oxford | 216/85 |
| 4,166,702 A | * | 9/1979 | Okamoto et al. | 399/57 |
| 4,243,883 A | * | 1/1981 | Schwarzmann | 250/343 |
| 4,570,069 A | * | 2/1986 | Gager | 250/343 |
| 4,740,709 A | | 4/1988 | Leighton et al. | 250/573 |
| 4,857,735 A | * | 8/1989 | Noller | 250/339.07 |
| 4,857,753 A | * | 8/1989 | Newburn-Crook et al. | 250/339 |
| 5,181,082 A | * | 1/1993 | Jeannotte et al. | 356/436 |
| 5,739,916 A | * | 4/1998 | Engelhaupt | 250/339.07 |

* cited by examiner

*Primary Examiner*—Randy Gulakowski
*Assistant Examiner*—Gentle E. Winter
(74) *Attorney, Agent, or Firm*—Christie, Parker & Hale, LLP

(57) ABSTRACT

A highly accurate sensor for monitoring the color density of various etchants in etchant regeneration systems is disclosed. The sensor comprises a Pyrex or equivalent tubular sensing chamber and a light cell housing surrounding a portion of the chamber. The chamber contains a rodlike extension extending into the interior of the chamber. The housing accommodates a light source, preferably an LED or laser, and a photodetector, optically coupled through an aperture in the housing. Two such sensors are used in a regeneration apparatus attached to an etching machine used for etching copper, iron, stainless steels or other materials. In another embodiment, multiple sensors are used to detect multiple constituents of the etchant depending on the material being etched and the etchant used. A system employing two sets of sensors is particularly applicable to etchants that pass one color of light well when fully regenerated and another color of light well when fully spent.

25 Claims, 4 Drawing Sheets

FIG.1
FIG.2
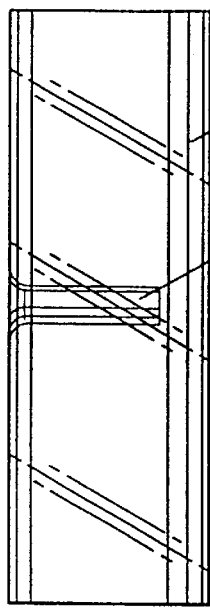
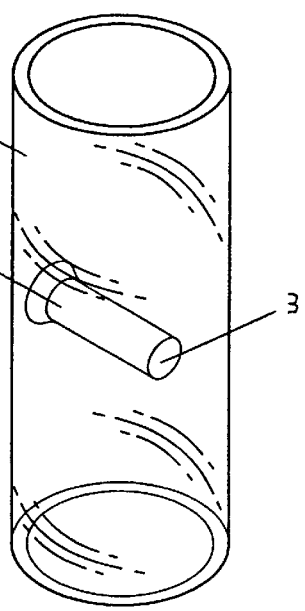
FIG.3
FIG.4
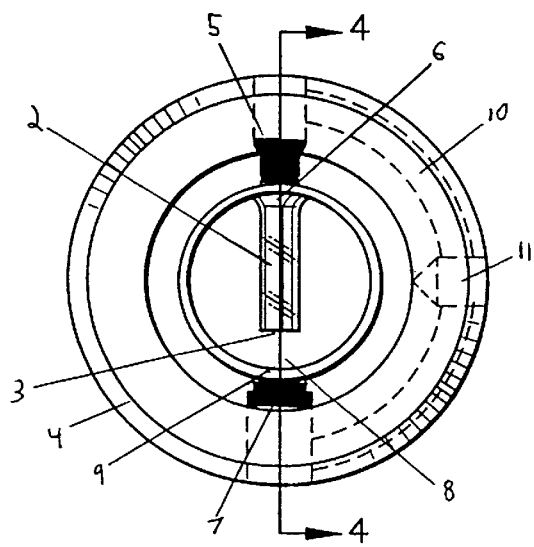
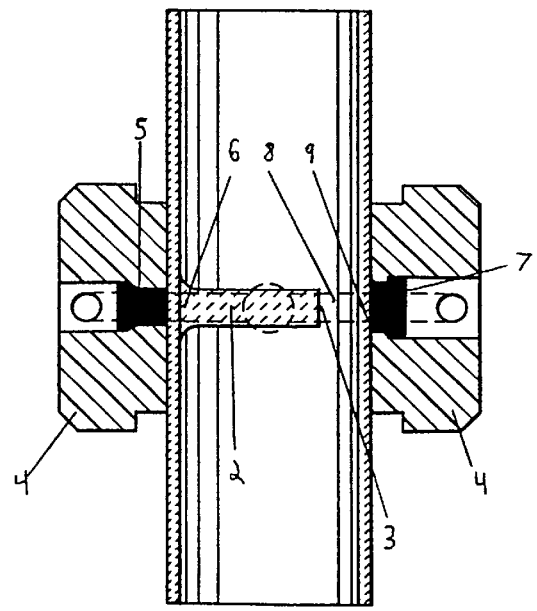

AUTOMATIC ETCHANT REGENERATION SYSTEM WITH HIGHLY ACCURATE SENSOR FOR MONITORING ETCHANT COMPOSITION

CROSS REFERENCE TO RELATED APPLICATIONS

This application claims priority of provisional patent application No. 60/146,100, filed Jul. 27, 1999, the contents of which are hereby incorporated by reference.

FIELD OF THE INVENTION

This invention relates generally to a system for regenerating an etchant, and more particularly to an apparatus and method for monitoring and manipulating etchant composition.

BACKGROUND

Cupric chloride and ferric chloride solutions are commonly used for etching copper and iron, respectively. Ferric chloride may also be used to etch stainless steel and alloys composed of iron and nickel. Although these etchants are quite effective in etching metal from the workpiece, the etching procedure becomes gradually less efficient. The etching process causes a continuous reduction of cupric ions ($Cu^{2+}$) to cuprous ions ($Cu^{1+}$), and ferric ions ($Fe^{3+}$) to ferrous ions ($Fe^{2+}$). Cuprous ions and ferrous ions are ineffective as etchants and retard the etching procedure as their concentration increases. Thus, the continuous accretion of cuprous or ferrous ions into the etching solution reduces the effectiveness of the etching process over time.

Cupric chloride and ferric chloride change color and clarity as their composition changes. A fresh solution of cupric chloride is a clear green color, but a spent solution, containing a substantial amount of cuprous chloride, turns opaque brown because cuprous chloride, being insoluble, forms a brownish precipitate. A fresh solution of ferric chloride is a clear red-amber color, but a spent solution, containing a substantial amount of ferrous chloride, is clear green.

To compensate for the gradual degradation of etching efficiency, prior art systems became available to regenerate the etchant. One such prior art system is disclosed in U.S. Pat. No. 4,132,585, commonly owned by the assignee of the present invention, the contents of which are hereby incorporated by reference. The '585 patent discloses an etchant regeneration system that monitors the composition of etchant solution withdrawn from an etcher to diagnose a component deficiency. A light sensor is responsive to the color density of light rays passing through the etchant. A first meter relay is responsive to the light sensor. If the color density of the etchant falls outside preset levels, a pump is energized causing addition of a constituent component into the etchant. A second light sensor senses the color density of the light rays passing through the etchant after the addition of the constituent component. A second meter relay is responsive to the second light sensor. If no improvement of the etchant color is detected, the second meter relay causes the discontinuance of the constituent component addition and switches to the addition of another constituent component, until the etchant is restored.

The conventional light sensor in the prior art system uses an incandescent light bulb for shining light through the wall of an acrylic pipe through which the etchant is flowing. The section of pipe where the light passes through the etchant is referred to as the sensing chamber. The light then passes out from the etchant, through the pipe wall opposite the light source, and strikes a detector. The detector measures the amount of light that penetrated the liquid.

Although effective for regenerating a certain amount of spent cupric chloride, the conventional sensor suffers from several disadvantages. First, the sensing chamber is made of acrylic. The ability of light to penetrate the acrylic varies from spot to spot, and the acrylic becomes cloudy over time. The detector and light source must therefore be calibrated frequently to account for these variables. The acrylic also has the tendency to diffuse the incoming light. Some of the incident light will therefore travel through the acrylic and reach the detector, rather than passing through the etchant flow as intended. Moreover, the acrylic is sensitive to changes in temperature. For example, in cold climates, the sudden change in temperature when the etcher is started may shatter the acrylic.

The size and shape of the sensing chamber in the prior art system also contribute to inaccuracy in the color density measurement. In one embodiment, the sensing chamber is about 15 mm in diameter to promote etchant flow through the regeneration system. Because the light from the light source must cross this distance before striking the detector, much of the light may become blocked in spent solutions. The blocking of incident light contributes to less accurate measurement of the transparency of the etchant except at low etchant concentrations, and limits the maximum concentration that may be measured.

Another disadvantage of the conventional sensor is its use of an incandescent bulb as the source of light. Incandescent, white light covers a wide range of wavelengths. Only specific wavelengths of light, however, are useful for monitoring the etchant in the sensing chamber. To pass a high intensity of light at a specific wavelength through the etchant, a very high intensity of incandescent light must be sent into the chamber. At very high intensity, an incandescent bulb generates so much heat that it damages over time both the acrylic tubing that surrounds the sensing apparatus, and the detecting device. Both types of damage lead to inaccuracy in the sensing system, and to the inefficient regeneration of the etchant.

The high intensity of incident white light also results in inaccurate detector operation. Stray light of wavelengths outside the ideal range may reach the detector to an inconsistent and unpredictable extent. The detector cannot distinguish between the stray light and the light within the range of appropriate wavelengths. To account for this discrepancy, the detectors must be frequently calibrated. However, because of the unpredictability of the amount of extra light reaching the detector, the calibration process is often difficult.

Another consequence of the relatively low intensity of light at suitable wavelengths is the inability of the sensor to operate above relatively low concentrations of metal copper in the etchant, and the inability of the sensor to operate at all with iron etchants. When less light in the specific wavelength band best transmitted by transparent etchant is sent into the liquid, less precipitate is required to completely block the light. This amount of precipitate is the most that can be accurately monitored. Because the amount of precipitate is roughly proportional to the amount of free metal in the solution, the concentration of metal copper is similarly restricted. The maximum concentration of copper that can be sensed in the conventional system is about 27 ounces per gallon of etchant.

Measurement of the transparency of ferric chloride requires the use of light in the red wavelengths. Incandescent bulbs produce only a low intensity of light in this wavelength region. To generate enough red light to monitor a substantial amount of ferric chloride, the incandescent bulb would have to be so bright that the heat generated by the incandescent bulb would destroy the sensor. Also, any green light would make the sensor useless. Therefore, the on-site regeneration of ferric chloride through the use of the conventional sensing system is not feasible. The regeneration of ferric chloride is currently accomplished via the trial-and-error addition of large quantities of acid and oxidizer at an off-site facility. The regenerated etchant is then resold to the etcher. The transportation of the deteriorated etchant to and from the recycling facility, and the measures required to do so safely, incur additional expense for the etcher.

The conventional detector also has various disadvantages. The detector opposite the bulb is a cadmium sulfide photocell, which has a tolerance as high as 200%. As a result, the two detectors in a given apparatus have to be matched to each other to obtain accurate operation of the regeneration system. Frequent recalibration of the detectors is required. Also, the detector is not sealed against contamination by gaseous chlorine or by solvents inside the acrylic pipe. The lack of protection requires frequent replacement of the detector.

SUMMARY OF THE INVENTION

The invention provides in one embodiment for a more accurate sensor for monitoring the color density of various etchants. The invention may be used in etchant regeneration machines, which add appropriate amounts of acid and/or oxidizer to the etchant based upon the measurements of the sensor. The etchant regeneration process uses material etched from a workpiece, and added acid and oxidizer to create more etchant. Excess etchant is then removed from the system and recycled.

In a presently preferred embodiment, a sensor for an etchant regeneration system comprises a Pyrex or equivalent tubular sensing chamber and a light cell housing surrounding a portion of the chamber. The sensing chamber may alternatively be made of another transparent heat resistant and durable material. Etchant is diverted into the chamber from a conventional etching system. The chamber contains a rodlike extension extending into the interior of the chamber. The housing accommodates a light source, preferably an LED or laser, and a photodetector, optically coupled through an aperture in the housing.

In alternate embodiments, the invention provides regeneration systems. Two sensors are used in a regeneration apparatus attached to an etching machine used for etching copper, iron, stainless steels or other materials. In another embodiment of the present invention, multiple sensors are used to detect multiple constituents of the etchant depending on the material being etched and the etchant used. A system employing two sets of sensors is particularly applicable to etchants that pass one color of light well when fully regenerated and another color of light well when fully "spent". In additional embodiments, more than two sets of sensors may be used to detect the presence of multiple etchant constituents.

BRIEF DESCRIPTION OF THE DRAWINGS

These and other features of the present invention will be better understood with reference to the following Detailed Description and the accompanying drawings, wherein:

FIG. 1 is a side view of the sensing chamber;

FIG. 2 is a view of the sensing chamber tilted slightly along vertical and horizontal axes;

FIG. 3 is a cross-sectional top view of the sensing chamber within the light cell housing;

FIG. 4 is a cross-sectional side view of the sensing chamber within the light cell housing. The cross-sectional axis for this illustration is indicated by line 4 in FIG. 3.

DETAILED DESCRIPTION

Figure 5:
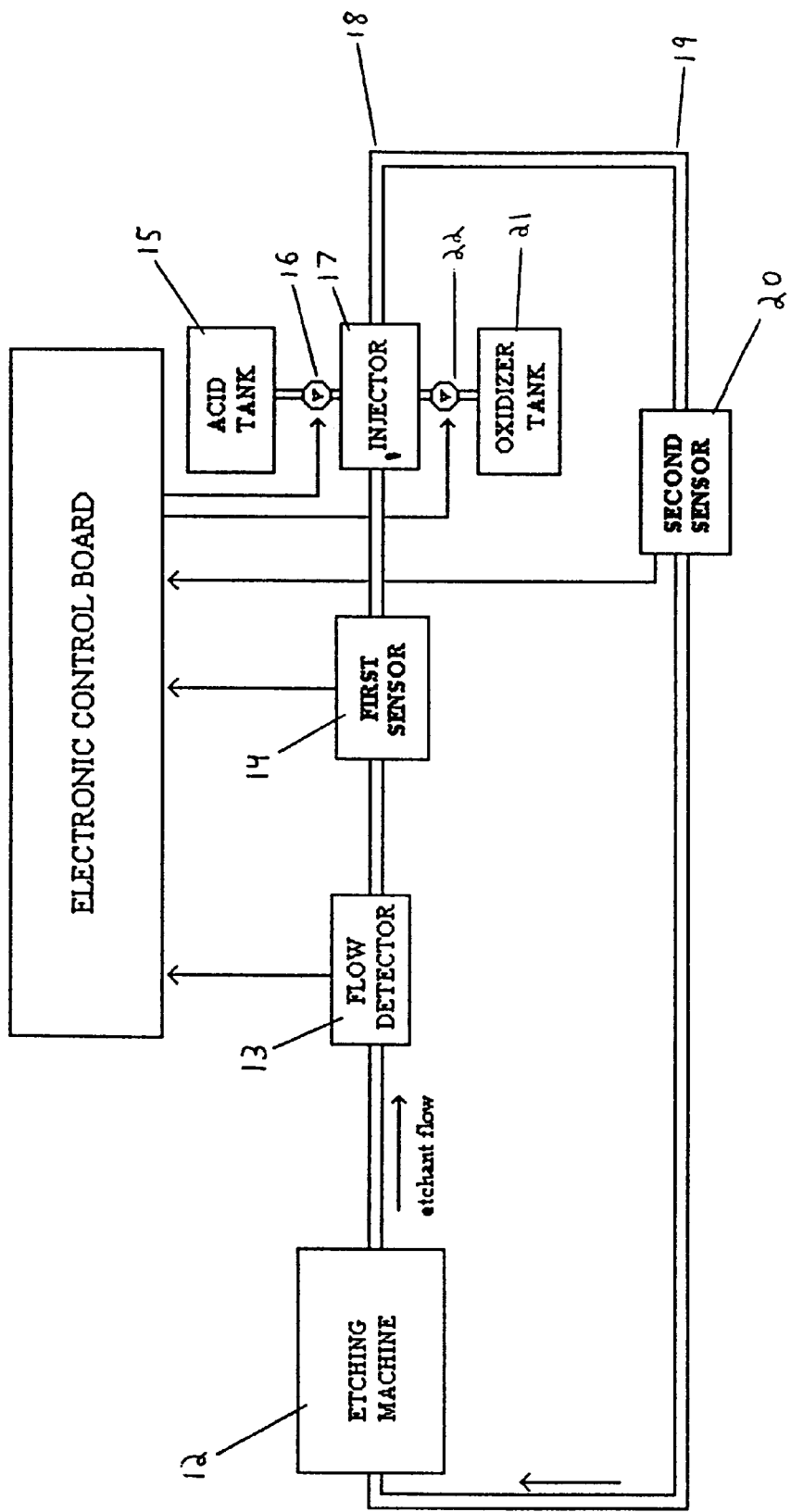
FIG. 5 is a schematic diagram of an automatic etching system, incorporating sensors according to the present invention.

The present invention can be used to regenerate etchant in any conventional etching system, including the system described in U.S. Pat. No. 4,132,585, the contents of which are hereby incorporated herein by reference. For example, as an etching process employing cupric chloride as an etchant generates cuprous chloride, the color density of the etchant changes (e.g., clarity and transparency decrease). As the etchant deteriorates through prolonged use, a sensor detects the change in composition of the etchant and initiates a series of reactions that rejuvenate the etchant.

An overview of one conventional embodiment of an etchant regeneration system is as follows. Some of the etchant is kept flowing through an etchant regenerating apparatus that incorporates two sensors. The etchant flows through a first sensor in the apparatus. If the first sensor measures enough transparency, nothing happens. However, if the transparency of the etchant is low enough, then the first sensor initiates the addition of acid in a reaction area, located downstream from the first sensor and upstream from a second, identical sensor. If the addition of acid improves the transparency of the etchant within a certain time, as determined by the second sensor, then the addition of acid continues until the first sensor measures enough transparency. However, if the transparency does not improve by that time, the addition of acid ceases and the addition of oxidizer begins. If the second sensor indicates improved transparency, oxidizer is added until the first sensor measures enough transparency. Once the first sensor detects that the transparency has been restored to within normal parameters, the addition of both acid and oxidizer ceases.

The present invention provides, among other features, novel sensors for greatly increasing the accuracy and efficiency of the conventional etchant regeneration process. In an exemplary embodiment of the invention, the sensor monitors the transparency of etchant using a Pyrex chamber 1 that serves as a sensing chamber utilizing the flow of a portion of etchant diverted from the etcher. Alternatively, the chamber may be made of any transparent material that is heat resistant and durable. The diameter of the chamber is preferably large enough to ensure enough flow of etchant through the system to regenerate the etchant in a reasonably short time. However, the diameter should be small enough to ensure that the light need not pass through an excessive volume of etchant, because larger volumes of etchant reduce the concentration of metal copper or iron in the etchant that the sensor can accurately monitor. The diameter of the chamber in a presently preferred embodiment is approximately 26 mm, but may be varied depending on the size of the etcher being used.

A rodlike extension 2 of the wall of the Pyrex chamber 1 extends into the interior area of the sensing chamber towards the opposite wall. The end 3 of the rodlike extension is a preselected distance away from the wall. 7 mm works well in most cases. The distance between the end of the rodlike extension and the wall is preferably not too great, otherwise the incident light must pass through too much etchant, thereby reducing the accuracy of the transparency measurement. However, if the distance is too small, then the presence of any small air bubbles in the etchant would interfere significantly with the transparency reading. In an embodiment of the present invention, the distance between the end of the extension and the opposite wall of the chamber is approximately ¼ inch. The distance between the end of the rodlike extension and the opposite wall of the chamber may be varied depending on the etchant used, the material being etched and the nature of the flow system by which the etchant is propelled through the sensor. The rodlike extension may be any shape and material that serves to direct light from the LED through the etchant and to the photodetector. In an embodiment of the present invention, the rodlike extension is made of Pyrex.

A light cell housing 4 surrounds the Pyrex chamber and houses the LED and photodetector. The light cell housing is preferably made of PVC material, and includes a radial cavity having mounts for the LED and photodetector at opposite ends of the sensing chamber. The sensing chamber is oriented in the light cell housing so that the LED 5 is directly adjacent to the base 6 of the rodlike extension of the sensing chamber. The photodetector 7 is mounted just behind the wall of the sensing chamber, directly across from the end 3 of the rodlike extension. This provides an optical coupling of light from the LED, through the rodlike extension, cavity, and etchant to the photodetector.

In the operation of the invention, light from the LED 5 is sent through the wall of the sensing chamber at the base 6 of the rodlike extension 2. The extension 2 acts as a fiber optic, channeling the light with minimal diffusion and avoiding the disadvantages incurred when the light must traverse the entire diameter of the sensing chamber. The light passes out of the end 3 of the extension, and then through the small volume 8 of etchant between the end 3 and the opposite wall 9. Whatever light is not absorbed by the etchant then reaches the detector 7. A space 10 within the light cell housing allows for electrical connections to the LED and photodetector, and the wiring reaches the exterior of the light cell housing via hole 11.

In one embodiment of the invention, the sensor is used in the regeneration of cupric chloride. In solution this compound forms complexes with water molecules. One of these complexes is yellow, and another is blue. The solution transmits light from about 460 nm to about 630 nm, with green light best transmitted. The best light to use in measuring transparency of such a solution is green, because changes in the concentration of cuprous chloride change the amount of green light transmitted through the etchant. In one embodiment, a Nichia NSPG500S LED is used as the light source. This LED produces light in the range of about 520 nm to about 545 nm, and operates at a power of 2000 to 4000 mCd, with a peak power of 6000 mCd. However, according to the principles of this invention, other LED sources in the green wavelengths may be used as well.

In another embodiment, the invention monitors the transparency of ferric chloride solution that is being used to etch Iron. Ferric chloride also forms complexes in aqueous solution. These complexes transmit light of wavelengths from about 570 nm to about 750 nm, and transmit red light best. Ferrous chloride, which is produced during the etching of iron, absorbs red light. Therefore, changes in the absorption of red light by the etchant are a good indicator of whether the etchant needs to be rejuvenated. In an embodiment, a Nichia NSPR500S is used. This LED produces light in the range of 650 nm to 670 nm, and operates at a power of 3000 to 5000 mCd, with a peak power of 5000 mCd. In another embodiment of the present invention, the light emitter has a power of 6,000 mCd, and a wavelength of 690 nm. In yet another embodiment of the present invention, a 3 to 4 milliwatt laser diode may be used. According to the principles of this invention, other LED sources in the red wavelength may be used as well.

It should be noted that other wavelengths of light may be suitable or desirable for use in detecting whether an etchant is spent depending on the color of the etchant. The color of the etchant may vary depending on the material being etched. For example, when iron is being etched with ferric chloride, as explained above, the absorption of red light of approximately 690 nm is a good indicator of whether the etchant is "spent". This is because the etching process generates ferrous chloride which absorbs red light of approximately 690 nm.

Alternatively, when 300 series stainless steel is being etched with ferric chloride, the absorption of infra-red light of approximately 880 nm is a good indicator of whether the etchant is "spent". This is because the etching of 300 series stainless steel generates $Cr^{+2}$ ion which absorbs light at approximately 880 nm, whereas $Cr^{+3}$ transmits infrared. Therefore, the more stainless steel etched, the more $Cr^{+2}$ ion in the etchant, and the less 880 nm light transmitted through the etchant from the light source to the photodetector. Thus, in an embodiment, an infrared sensor for measuring the presence of chromium employs an 880 nm LED with a power of 4,000 mCd.

In an additional embodiment of the present invention, multiple sensors are used to detect multiple constituents of the etchant depending on the material being etched and the etchant used. For example, in etching Fe Ni alloys, such as Fe Ni Alloy 42 or 52, two sets of sensors are used. One set of sensors is for sensing the presence of ferrous chloride, and the other set of sensors is for sensing the presence of ferric chloride. In additional embodiments sensors for light of different wavelengths than those specified above may be used depending on the etchant being used and the material being etched. A system employing two sets of sensors is particularly applicable to etchants that pass one color of light well when fully regenerated and another color of light well when fully "spent". In additional embodiments, more than two sets of sensors are used to detect the presence of multiple etchant constituents.

The invention solves many of the problems that exist with the conventional system. Pyrex glass does not become obscure over time. There is less variation in the ability of light to pass through Pyrex, and light is less likely to diffuse through the Pyrex around the etchant. Also, Pyrex glass offers greater resistance to temperature changes and to extreme cold or heat. The rodlike extension within the sensing area of the chamber improves the accuracy of the monitoring and allows higher concentrations of metal in the etchant to be run through the instrument. Because the end of the extension is relatively near to the opposite wall of the chamber, behind which the detector is located, the light must penetrate a smaller amount of precipitate in the etchant. This feature of the invention increases the accuracy of the color density and/or turbidity reading within the metal concentrations at which the conventional sensor functions. More importantly, the maximum concentration of metal in the etchant that may be accurately controlled has increased. For example, the maximum quantity of copper per gallon of etchant which may be accurately controlled has increased from 24–27 to 31–34 ounces per gallon. Furthermore, the use of the rodlike extension, in concert with the Pyrex material, greatly reduces inaccuracy due to stray light diffusing the walls of the chamber, rather than passing through the etchant inside the chamber, to the detector.

The invention's use of an LED in combination with the Pyrex tube has also solved many serious problems. Unlike the incandescent bulb, the output of the LED does not decrease over time. Because the LED shines specific wavelengths of light at much greater intensities than incandescent bulbs, the ability to penetrate the etchant for measurement of the color density is improved. The high intensity of wavelength-specific light greatly increases the maximum concentration of metal in the etchant that can be accurately monitored. Moreover, the LED achieves high intensity light with much less heat output than an incandescent bulb. Thus, the detector and the pipes surrounding the sensor have a longer lifetime. In addition, the risk of stray light of wavelengths outside the specific band for that metal reaching the detector is minimal, due to the great specificity of light that an LED makes possible. As a result, appropriate calibration of the detector need only be done once or relatively few times in the lifetime of the sensor.

The use of an LED in the invention has made possible for the first time the regeneration of ferric chloride in the same apparatus where the etchant is being used, rather than at an off-site facility. The incandescent bulb produced very little red light, so that monitoring the etchant accurately would require such bright incandescent light that the heat generated would destroy the sensor and surrounding acrylic pipe. However, a red LED provides as high as 50 times as much light in the desired wavelengths. Coupled with a more sensitive photodetector, the regeneration of ferric chloride may be done in the same way as cupric chloride regeneration, without the costs associated with off-site regeneration.

The photodetector solves many problems in accuracy and calibration. The tolerance of this detector is much smaller than that of the cadmium sulfide photocell. Also, the photodetector is hermetically sealed to prevent the detection of stray light or contamination by PVC solvent. Therefore, the photodetector offers improved accuracy and need only be calibrated once or relatively few times in the lifetime of the sensor.

Possible light sources include blue LEDs, blue/green LEDs, green LEDs, red LEDs, red laser diodes, infrared LEDs and infrared laser diodes. Possible light receivers for use in light detection include: CdS photo resistors, CdSSe photo resistors, CdSe photo resistors, pin photo diodes, charge coupled devices, and NPN photo transistors.

In one embodiment for etching copper and iron, a Clairex CL704L photodetector is used. According to the principles of this invention, any similar photodetector with similar or lower tolerance, comparable sensitivity at the wavelength of the LED being used, and capable of being hermetically sealed may be used. The Clairex CL704L has a peak sensitivity at 690 nm and operates at a working voltage range of 4 to 12 V.

A scale of light transmission through the etchant is calibrated from 0 to 100, with 0 correlating to 100% absorbance by the etchant, and 100 correlating to 100% transmission through the etchant. In an embodiment of the present invention, this scale is obtained by measuring the minimum and maximum output of the photodetector. A scale of output of the photodetector is then created with threshold values triggering certain events as described below.

In one application, the invention is used in a regeneration apparatus that is attached to the etching machine. The apparatus oxidizes the cuprous or ferrous forms back into the cupric or ferric forms, thus reinvigorating the etchant. While the etching machine is in operation, it continuously pumps the etchant into the regeneration apparatus for monitoring. The flow of etchant first enters a flow detector 13, which electronically enables a time delay in which bubbles are expunged from the liquid. The flow detector also triggers a relay which provides power to the regeneration apparatus, so that the regeneration apparatus does not operate when no flow of etchant is entering the system.

In a first embodiment, the flow of etchant enters a first sensor 14, that continuously monitors the composition of the etchant. If the transparency of the etchant is above a certain minimum, no action occurs. If the transparency falls below a certain level, the first sensor electronically triggers the addition of hydrochloric acid from an acid tank 15. A valve 16 adds the acid to the etchant flow in the injector 17. The passage of the etchant through the injector 17 creates a negative pressure, pulling the acid into the etchant flow. The addition of acid provides the extra hydrogen needed to react with excess sodium chlorate, if any. The regeneration of etchant works best if two elbows 18 and 19 are used as the reaction area, where the added components are thoroughly mixed with the etchant. The etchant then flows to a second sensor 20. If the second sensor detects a significant change in color density (e.g., an increase in transparency) of the etchant within a predetermined period, say, seven seconds, more acid is added. If the second sensor does not detect a significant increase in transparency, acid addition stops and addition of sodium chlorate oxidizer from its tank 21 occurs through another valve 22. Because the addition of acid may necessitate the addition of more oxidizer, and vice versa, the regeneration cycle usually repeats several times. The regenerated etchant returns to the etching machine.

Figure 6:
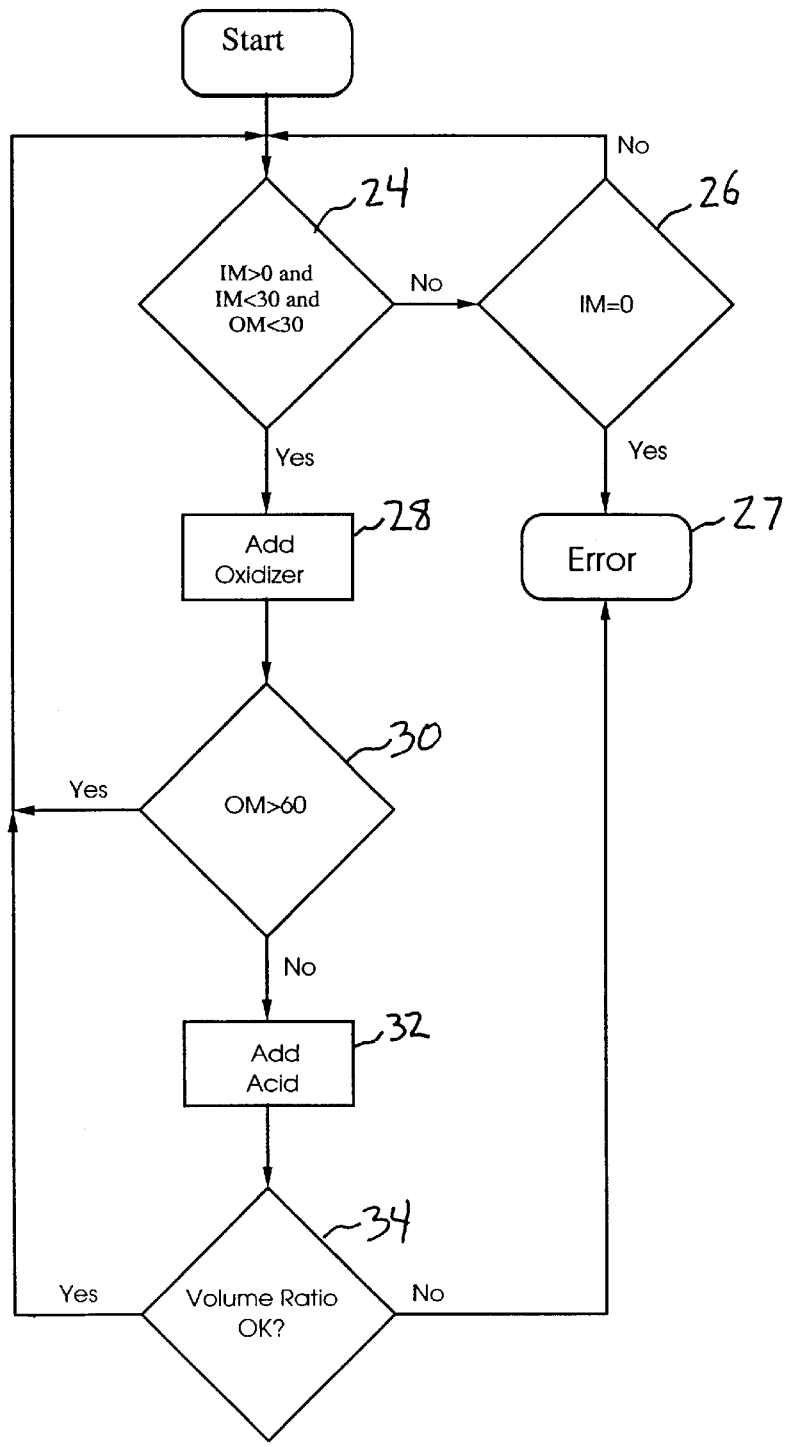
FIG. 6 is a flowchart indicating the steps of an automatic etchant regeneration system according to an embodiment of the present invention.

In a second embodiment of the present invention, shown in FIG. 6, the etchant is used for etching iron and stainless steels, such as 304 stainless steel. The apparatus is structured the same as in the first embodiment. The etchant passes through a first sensor, known as an input sensor, an injector, and a second sensor, known as an output sensor.

In a first step (Step 24), the system checks the light transmission at the input and output sensors. The system initially asks whether some light is passing through the etchant to the input sensor and whether the amount of light detected by the input and output sensors is below a first threshold. If the light detected is below the first threshold then the etchant needs to be regenerated.

If the answer to the first question is false, this is either because the input sensor did not receive any light through the etchant or because the amount of light sensed is above the first threshold. In order to determine which of these two situations is applicable, the system asks whether any light is being transmitted to the input sensor (Step 26). If the input sensor indicates that no light is being transmitted through the etchant, then the system assumes that there is an error in the light source, photodetector, or etchant concentration and summons help, (Step 27). Alternatively, if the input sensor indicates that some light is passing through the etchant, then the system knows that the etchant does not need regeneration, resets, and asks the initial question again. The above cycle may occur numerous times in one second. In one embodiment of the present invention, the cycle is repeated 15 times in one second if no need for regeneration is observed through the sensors.

If the answer to the first question is true, meaning some light is being transmitted to each sensor, but an amount that indicates that the etchant needs to be regenerated, then the system proceeds to regenerate the etchant. The system adds a volume of oxidizer (Step 28), and waits for a predetermined amount of time, approximately 10 seconds, for example while checking the reading at the output sensor (Step 30). If the output sensor reads above a second threshold amount, thus indicating that the etchant has been regenerated, then the system resets and returns to the first step. If the output sensor does not read above the second threshold amount, then the system adds a volume of acid (Step 32), waits for another predetermined sample delay time, approximately 10 seconds for example, while checking the output sensor. The system continues to add acid until the input sensor reads above the second threshold amount, or until a maximum value of acid has been added.

Once the input sensor reads above the second threshold amount, or once a maximum amount of acid has been added, the system compares the volume of acid added with the volume of oxidizer added (Step 34). If the ratio of acid to oxidizer is outside of normal for the alloy being etched and the concentrations of reagents used, then the system presumes that there is an error in the system and summons help (Step 27). If the ratio of acid to oxidizer is within the normal range for the alloy being etched and the concentrations of reagents used, then the system returns to the first step and begins the procedure over again.

Figure 7:
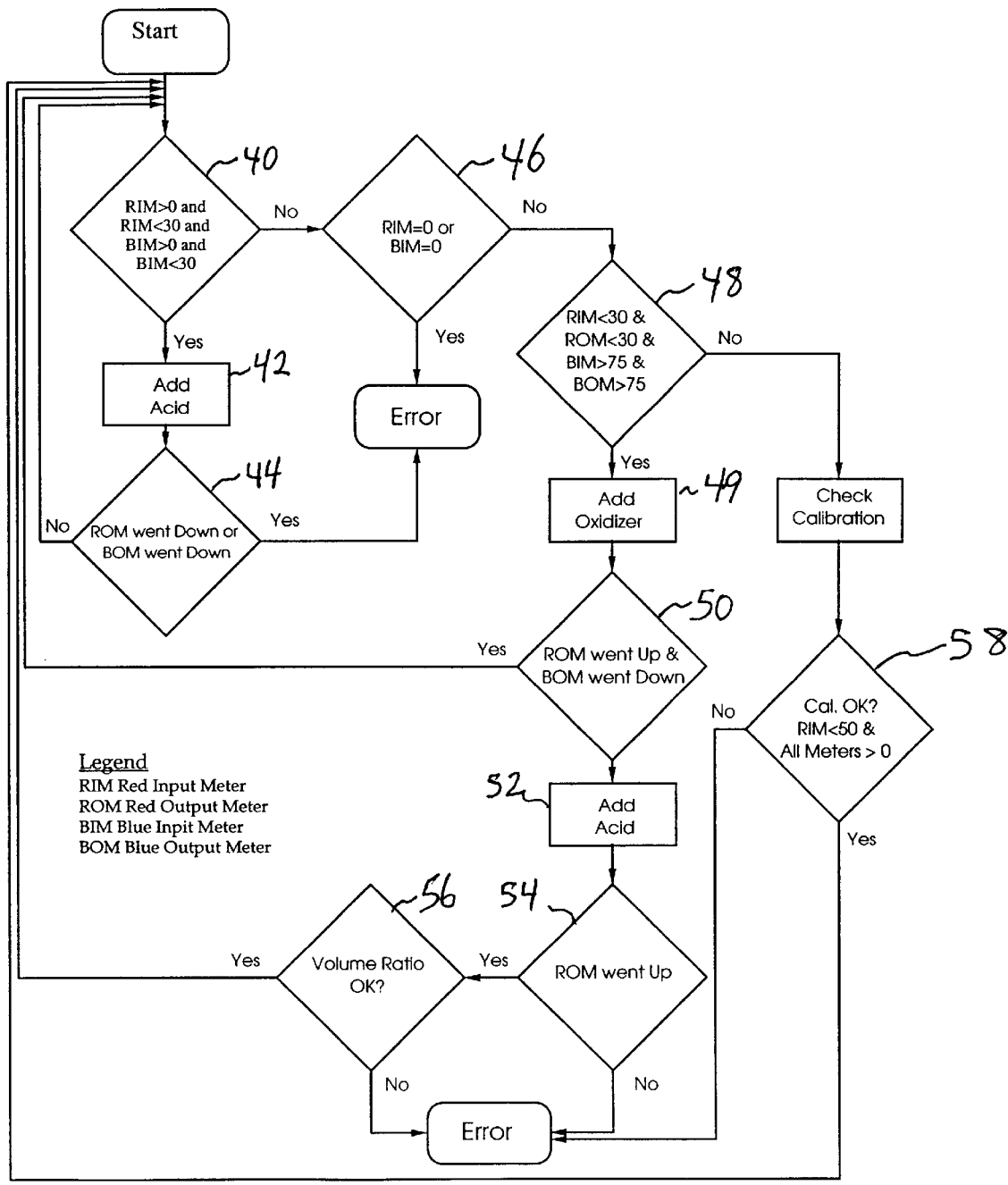
FIG. 7 is a flowchart indicating the steps of an automatic etchant regeneration system according to an embodiment of the present invention.

In a third embodiment of the present invention, shown in FIG. 7, the etchant is used for etching Alloy 42 or 52 Fe Ni. The apparatus is structured so that the etchant passes through two input sensors, an injector, a mixing chamber, and two output sensors. In this embodiment, a pair of conventional 6 inch static mixers may be used. A first input sensor is the red sensor that was previously described for detecting red light levels associated with ferrous chloride, known here as the "red input sensor". A second input sensor is a green sensor for detecting green light absorbed by ferric chloride, known here as the "green input sensor". Likewise, a first output sensor is a red sensor and a second output sensor is a green sensor, known here as the "red output sensor" and the "green output sensor" respectively. The third embodiment takes advantage of the fact that when Alloy 42 or 52 Fe Ni is etched, the etchant changes color absorption with respect to both red and green light. As the etchant is spent, the amount of green light absorbed by the etchant decreases, and the amount of red light absorbed by the etchant increases. The input sensors preferably monitor the etchant transparency many times per second.

The first question asked by the system is whether some light is detected by both input sensors and whether the amount of light detected by both input sensors is below a first threshold amount (Step 40). If the answer to the first question is true, then the etchant is assumed to need acid and a volume of acid is added to the etchant (Step 42). Once the volume of acid is added, the system waits for a predetermined sample delay time which is set according to the mechanical layout of the machine and the time that it takes the liquid to move to the mixing chamber where it reacts, and then to flow to the sensor, for e.g. 10 seconds, while testing both output sensors (Step 44). The sample delay time may range, for example, from 7 to 30 seconds. If either of the output sensors receives less light through the etchant than before the addition of the acid, the system assumes an error is present and summons help. If either output sensor detects more light through the etchant after the addition of the acid, or if both sensors detected the same amount of light through the etchant both before and after the addition of the acid, then the system resets and re-asks the first question.

Alternatively, if the answer to the first question is false, then the system checks if either input sensor indicates that no light is being transmitted through the etchant (Step 46). If either input sensor indicates that no light is being transmitted through the etchant, then the system assumes that an error exists and summons help. If both input sensors indicate that light is being transmitted through the etchant, then the system asks whether the amount of light detected by the red input and output sensors is below the first threshold and whether the amount of light at the green input and output sensors is above a second threshold (Step 48).

If the red input and output sensors indicate light below a first threshold and the green input and output sensors indicate light above a second threshold, then the system adds a volume of oxidizer (Step 49). After the system begins adding oxidizer, the system waits 10 seconds, then measures the light levels of the output sensors (Step 50). If the red output sensor detects more light being transmitted through the etchant, and the green sensor detects less light being transmitted through the etchant, then the system assumes that the etchant has been regenerated, resets, and returns to the first question. If the red output sensor did not go up, or the green output sensor did not go down, then the system adds acid (Step 52). The system waits for a predetermined sample delay time for the fluid to mix and reach the sensors, e.g., 10 seconds or so, depending on the size of the etcher, while checking the red output sensor to see if more light is transmitted through the etchant (Step 54). If the red output sensor does not detect more light through the etchant after the addition of the acid, then the system assumes that an error is present and summons help. If the red output sensor does detect more light through the etchant after the addition of the acid, then the system checks the ratio of acid added to oxidizer added (Step 56). If the ratio of acid to oxidizer is outside of normal for the alloy being etched and the concentrations of reagents used, then the system assumes that there is a an error and summons help. If the ratio of acid to oxidizer added is inside of the normal range for the alloy being etched and the concentrations of reagents used, then the system resets and returns to the first question.

If both input sensors are indicating light transmission, the red input and output sensors are showing light transmission greater than a first threshold and the green input and output sensors are showing light transmission less than a second threshold, then the system checks the calibration of the sensors (Step 58). If the calibration of the sensors is okay, namely if the red input sensor is receiving light beyond a third threshold and all sensors are receiving some light through the etchant, then the system resets, and returns to the first question. If the calibration is not okay, because either the red input sensor is receiving a level of light below the third threshold, or one of the sensors is not receiving any light through the etchant, then the system assumes that an error is present and summons help.

The apparatus that has been disclosed provides a highly accurate, reliable, and cost-effective means for continuously monitoring the color density of etchant from an etching machine. The apparatus also provides more efficient and safe on-site generation of cupric chloride, and makes possible the on-site regeneration of ferric chloride as well. Furthermore, the apparatus makes possible the regeneration of any metallic chloride etchant that undergoes oxidations in a manner analogous to cuprous and ferrous chloride, and which in depleted form loses its transparency to an extent proportional to the accumulation of the undesired ions.

Those of ordinary skill in the art will understand that various modifications may be made to the embodiment without departing from the spirit and scope of the invention. The present invention may be used, for example, in conjunction with etching systems for etching transition metals chromium through copper in which the etchant is of the same composition as the material being etched. The system described herein is fully scalable, and therefore the described dimensions and delay periods may change depending on, for example, the amount of enchant that flows through the system and the size of the etching system. Furthermore, the specific wavelengths described are merely exemplary and may be changed depending on component availability and the characteristics of the particular etchant or etching process being used.

What is claimed is:

1. A sensor for detecting the composition of an etchant comprising:
    a sensing chamber;
    a light source coupled to a first side of the sensing chamber;
    a light source extension having a first end and a second end, the first end being coupled to the light source, and the second end extending substantially into the sensing chamber to optically guide light emitted by the light source through at least a portion of the etchant in said sensing chamber to a light detector coupled to a second side of the sensing chamber.

2. The sensor of claim 1 wherein the sensing chamber comprises borosilicate glass.

3. The sensor of claim 1 wherein the sensing chamber comprises a cylindrical tube.

4. The sensor of claim 1 wherein the light source comprises a Light Emitting Diode.

5. The sensor of claim 1 wherein the light source comprises at least one of the group consisting of a blue LED, a blue/green LED, a green LED, a red LED, a red laser diode, an infrared LED, and an infrared laser diode.

6. The sensor of claim 1 wherein the light detector comprises at least one of the group consisting of a CdS photo resistor, a CdSSe photo resistor, a CdSe photo resistor, a pin photo diode, a charge coupled device, and an NPN photo transistor.

7. The sensor of claim 1 wherein the light source comprises a light emitting diode having a wavelength of approximately 520 to 545 nm.

8. The sensor of claim 1 wherein the light source comprises a light emitting diode having a wavelength of approximately 650 to 690 nm.

9. The sensor of claim 1 wherein the light source comprises a light emitting diode having a wavelength of approximately 880 nm.

10. A sensor as provided in claim 1, further comprising a housing coupled to the light source, the sensing chamber, and the light detector; the housing sealing the sensor and interior of the sensing chamber from outside light.

11. A system for regenerating chloride etchant comprising:
    an etchant flow pipe;
    a first sensor coupled to the etchant flow pipe;
    an oxidizer input coupled to the etchant flow pipe;
    an acid input coupled to the etchant flow pipe; and
    a second sensor coupled to the etchant flow pipe;
    wherein the first and second sensors comprise
        a sensing chamber,
        a light source coupled to a first side of the sensing chamber,
        a light source extension having a first end and a second end, the first end being coupled to the light source, and the second end extending substantially into the sensing chamber to optically guide light emitted by the light source through at least a portion of the etchant in said sensing chamber to a light detector coupled to a second side of the sensing chamber.

12. The system of claim 11 wherein the etchant comprises at least one of the group consisting of cupric chloride and ferric chloride.

13. The system of claim 11 wherein material etched by the etchant comprises at least one of the group consisting of transition metals chromium through copper.

14. The system of claim 11 further comprising hydrochloric acid coupled to the acid input.

15. The system of claim 11 further comprising sodium chlorate oxidizer coupled to the oxidizer input.

16. The system of claim 11 wherein the light source comprises at least one of the group consisting of a blue LED, a blue/green LED, a green LED, a red LED, a red laser diode, an infrared LED, and an infrared laser diode.

17. The system of claim 11 wherein the light detector comprises at least one of the group consisting of a CdS photo resistor, a CdSSe photo resistor, a CdSe photo resistor, a pin photo diode, a charge coupled device, and an NPN photo transistor.

18. The system of claim 11, wherein the light source comprises an LED which produces a narrow beam of light at a wavelength corresponding to green light, and the etchant comprises cupric chloride.

19. The system of claim 11, wherein the light source comprises an LED which produces a narrow beam of light at a wavelength corresponding to red light, and the etchant comprises ferric chloride.

20. A sensor for detecting the composition of an etchant comprising:
    a sensing chamber;
    a light source coupled to a first side of the sensing chamber; and
    a light source extension coupled to said light source for propagating light transmitted by said light source a predetermined distance into said sensing chamber; and
    a light detector coupled to a second side of the sensing chamber for receiving light propagated by said light source extension.

21. The sensor of claim 20 wherein the light source comprises a Light Emitting Diode.

22. The sensor of claim 20 wherein the light source comprises at least one of the group consisting of a blue LED, a blue/green LED, a green LED, a red LED, a red laser diode, and an infrared LED with a wavelength in a range of 700–1000 nm.

23. The sensor of claim 20 wherein the light detector comprises at least one of the group consisting of a CdS photo resistor, a CdSSe photo resistor, a CdSe photo resistor, a pin photo diode, a charge coupled device, and an NPN photo transistor.

24. The sensor of claim 20 wherein the light source comprises a light emitting diode having a wavelength of approximately 520 to 545 nm.

25. The sensor of claim 20 wherein the light source comprises a light emitting diode having a wavelength of approximately 650 to 690 nm.

* * * * *